United States Patent [19]

Skow

[11] Patent Number: 5,628,735
[45] Date of Patent: May 13, 1997

[54] SURGICAL DEVICE FOR WICKING AND REMOVING FLUID

[76] Inventor: Joseph I. Skow, 16005 87th St. South, Hastings, Minn. 55033

[21] Appl. No.: 584,336

[22] Filed: Jan. 11, 1996

[51] Int. Cl.⁶ ............................ A61M 25/00; A61M 1/00
[52] U.S. Cl. ...................... 604/317; 604/268; 604/902
[58] Field of Search .................................. 604/313, 317, 604/323, 902, 268, 356

[56] References Cited

U.S. PATENT DOCUMENTS

| | | | |
|---|---|---|---|
| 3,324,855 | 6/1967 | Heimlich | 128/269 |
| 3,394,702 | 7/1968 | Heimlich et al. | 128/269 |
| 3,520,300 | 7/1970 | Flower, Jr. | 604/902 |
| 3,608,946 | 9/1971 | Erickson | 604/902 |
| 4,525,166 | 6/1985 | Leclerc | 604/313 |
| 4,533,352 | 8/1985 | Van Beck et al. | 604/317 |
| 4,790,833 | 12/1988 | Schmidt | 604/317 |
| 5,034,006 | 7/1991 | Hosoda et al. | 604/317 |
| 5,437,651 | 8/1995 | Todd et al. | 604/317 |

Primary Examiner—John G. Weiss
Assistant Examiner—David J. Cho
Attorney, Agent, or Firm—Joel D. Skinner, Jr.

[57] ABSTRACT

A flexible, sterile, trimable device which gently and continuously removes unwanted fluid from an operating field during surgery by wicking the fluid into a mat having a high wicking property. A flexible suction tube having one end embedded in the mat removes fluid from the mat, thereby preventing the mat from becoming saturated. One embodiment of the invention is as a surgical swabber where one end of a length of semi-rigid tube is embedded in the mat and the other end is connected to a flexible suction tube. Another embodiment of the invention is as a platform for microsurgery where a membrane having a plurality of holes is applied to one side of the mat. The membrane supports the tissue being worked on and is preferably a contrasting color. Fluid passing into the holes is wicked into the mat where it is subsequently removed by the suction tube. The platform can be oriented in any position and does not slip on the tissue on which it is placed. Another embodiment of the invention is as a device that seals off the nose from the throat during nasal surgery so that blood from the nasal procedure will not go down the back of the throat. A nonporous sheet of silicone rubber or similar material is applied to one side of the mat. The sheet is sufficiently thick to give the device a springy quality which allows the device to be folded in half longitudinally then deploy into an inverted V configuration in the nasal cavity.

6 Claims, 3 Drawing Sheets

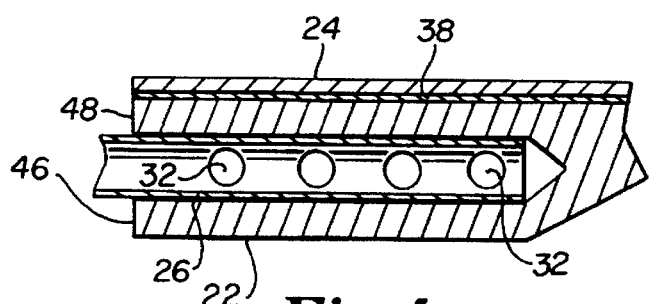
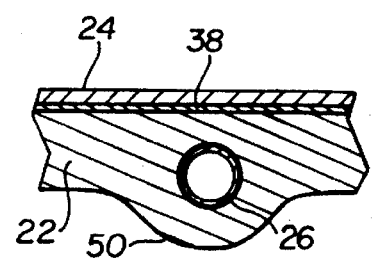
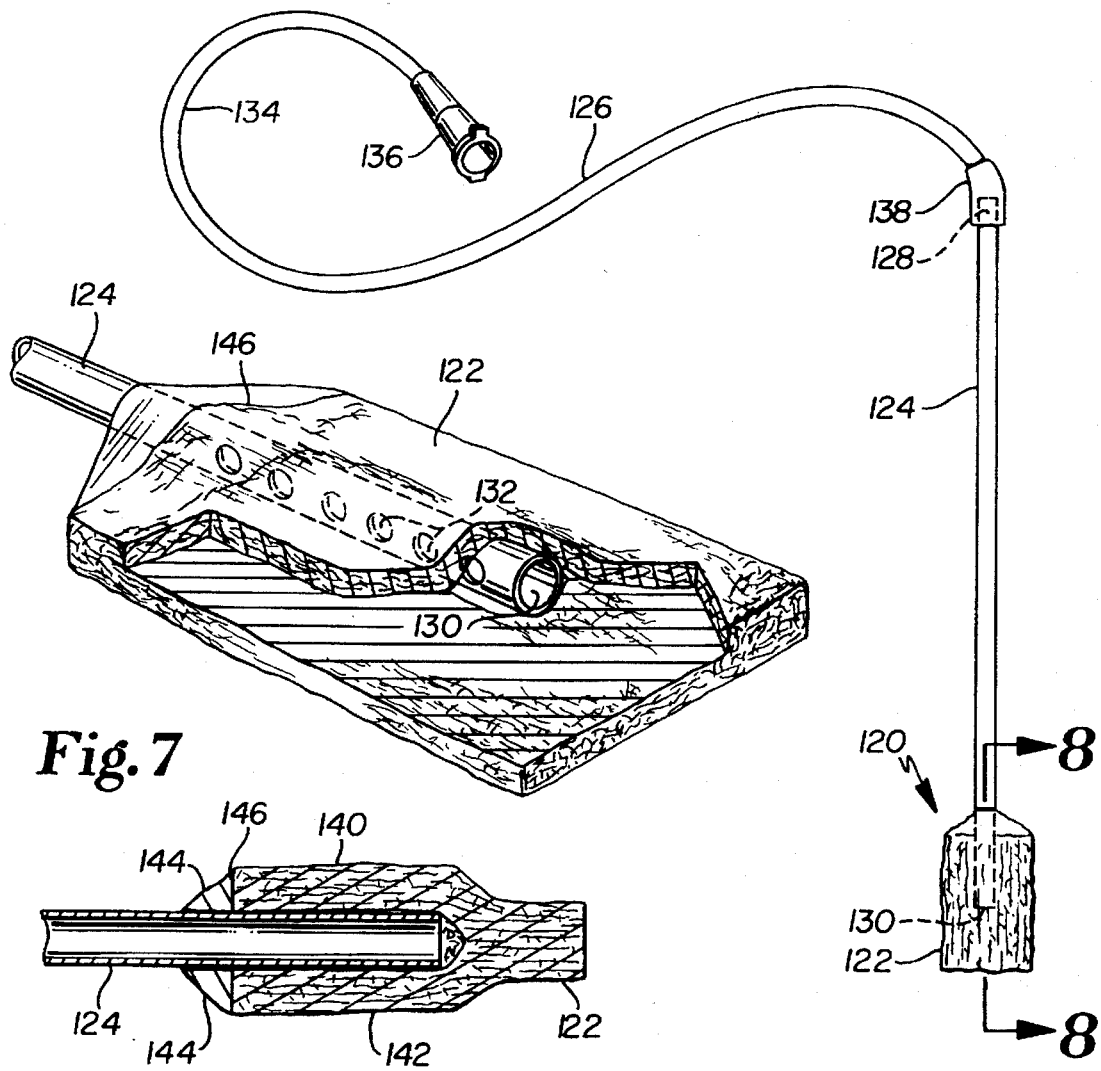

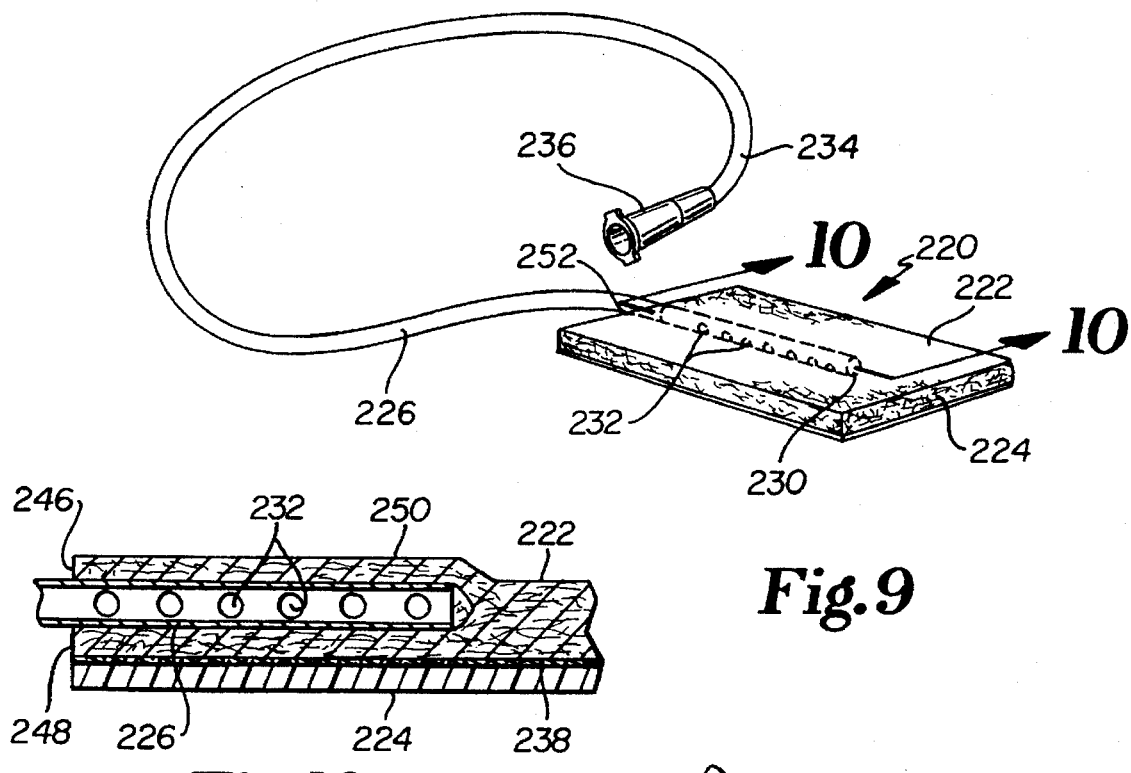
Fig. 9
Fig. 10
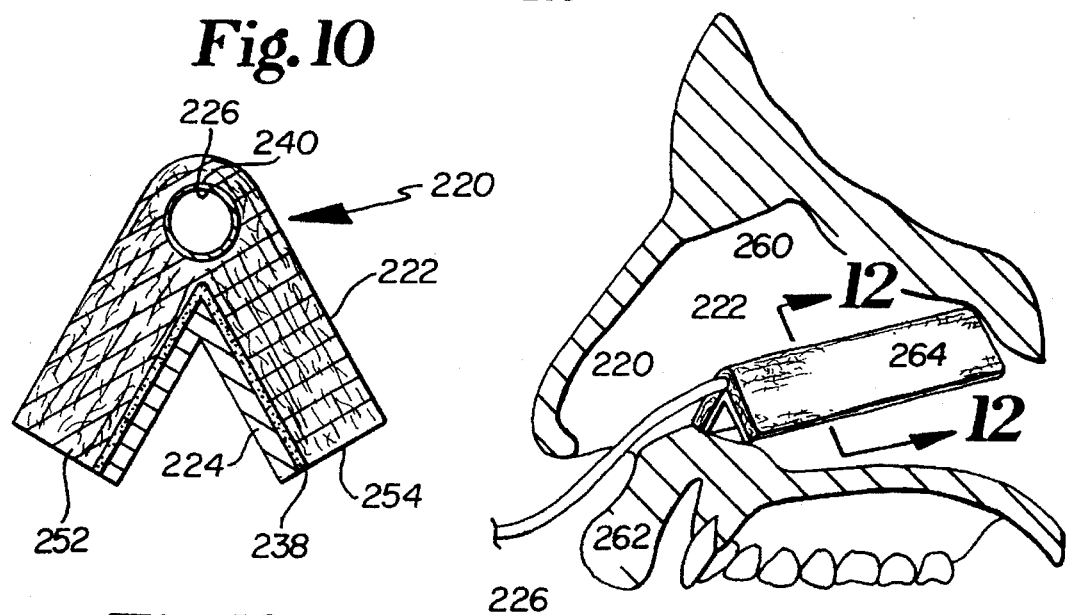
Fig. 12
Fig. 11

SURGICAL DEVICE FOR WICKING AND REMOVING FLUID

BACKGROUND OF THE INVENTION

1. Field of the Invention

The present invention pertains generally to medical devices. More particularly, the invention relates to devices for removing fluid from a predetermined area during surgery. The apparatus and methods provided by the invention are especially useful for microsurgery and nasal surgery.

2. Background Information

During surgery, unwanted fluids must be evacuated from the operating field. For large field surgery hi the chest, abdomen or pelvis for example, this is often done by using a suction tube placed directly in pooled fluid such as blood. In microsurgery, however, because tissues affected are very small and delicate, use of direct suction even with a very small cannula and very low power can cause significant damage to, and even total destruction of, tissue exposed to the direct suction.

In large field surgery, fluid is also removed with sponges mounted on handles such as disclosed in U.S. Pat. No. 1,853,238 to Shields and U.S. Pat. No. 2,294,186 to Kirschbaum. Similar sponge sticks with hollow handles can be attached to a suction source as disclosed in U.S. Pat. No. 3,324,855 and U.S. Pat. No. 3,394,702 to Heimlich. All those devices are relatively large and designed to be grasped with a hand. They are not suitable for microsurgery where smaller workspace requires smaller tools, and quantities of fluid removed are smaller. Furthermore, to absorb liquids, those devices use gauze or elastomeric sythetic foam sponge for example. Because of their coarseness, these materials can damage delicate tissue typically involved in microsurgery when the materials contact these tissues. Therefore, these devices are not well suited for microsurgery.

To remove fluid during microsurgery, a small swab on a stick is often used. Swabs on a stick were disclosed in U.S. Pat. No. 3,179,108 to Block et at. Swabs used for microsurgery typically have an elongated triangular shape and are made of cellulose, for example. These are commonly called eye spears because the triangular shaped swab mounted on a 2" long shaft resembles a spear. A device sold under the trade name WECK-CEL is typical of those devices. Such a swab is small enough to be handled by the surgeon's fingers and fit in most areas of the body where microsurgery is performed. However, multiple swabs are needed to remove fluid in a typical microsurgery procedure since each swab quickly saturates and must be replaced. Besides using several swabs, the repeated removing of the saturated swab and replacing it with a dry one takes significant time and diverts the attention of the surgeon from the subject procedure, which is neither safe nor efficient.

Microsurgery presents another problem not typical in large field surgeries. Micro surgery is typically done on very small blood vessels, nerves, or other tissue which are delicate and often require a background mat or platform on which to rest these tissues during surgery. Prior art platforms or backgrounds often become basins that catch unwanted fluids, such as blood, which makes such surgery more difficult than if the platforms were clear of unwanted fluids. It is also not desirable to have to intermittently swab the platform during an operation to keep it clear of unwanted fluid.

U.S. Pat. No. 4,533,352 to Van Beek et at. discloses a flexible silicone rubber platform which incorporates suction in it. One embodiment of Van Beek's platform has a plurality of ribs and troughs with a hole in each trough connecting to a suction tube. The ribs support the tissue being worked on and the troughs allow fluid to flow in them to the hole where it is sucked away. In another embodiment, the tissues being worked on is supported by a porous pliable material. The porous pliable material has a synthetic coating on its bottom and sides.

Drawbacks of both of Van Beek's platforms include that they rely on gravity to conduct fluid to the suction holes. Therefore, they must be positioned so that fluid can move by gravity (rubber) or by direct suction (porous) to the holes. This significantly limits the positions in which the platforms can be used. Also, Van Beek's platforms have a rubber or plastic surface on the bottom which may be prone to becoming slippery when in contact with fluid, and which may allow the platform to slide on the tissue on which it is placed.

A further drawback of the Van Beek embodiment having a porous member with a synthetic coating on its edges is that the platform is not suited for trimming to fit a desired size or shape. Any trimming would remove a section of the coating on the edge which would allow the platform to "leak". While it is possible to recoat the edges after trimming, it is not practical to do so. An alternative but expensive solution is to make the platform in a great many predetermined geometrical shapes and sizes.

Another prior art platform is the TEBBETTS™ SOFT SUCTION MATT™ manufactured by Applied Medical Technology, Inc. That platform has a nonperforated membrane applied to a polyurethane foam pad which is approximately 1.5 mm thick. A suction tube having a plurality of holes is attached between the membrane and the foam pad. The Tebbetts device is used with the membrane side down while the tissue being worked on rests on the foam.

A drawback of the Tebbetts device is that it can be used in only limited orientations. Because the polyurethane foam has very poor wicking ability, the device only works by pooling fluids in the foam above the membrane. The polyurthane foam is open-cell and acts as a conduit for fluid to flow to the suction tube. The device can be shaped to allow such pooling, but it does not work well in orientations which do not allow gravity to drain fluid toward the suction tube.

Another drawback of the Tebbetts device is that it slips. There is no mechanism to remove fluid which accumulates between the membrane and the tissue against which it is placed, so the device can slip on the accumulated fluid.

A further drawback of the Tebbetts device is that it has no color. When blood pools in the foam pad, the pad turns red which makes it difficult to distinguish the tissue being worked on from the pad.

During nasal surgery, it is desirable to keep blood from the operation environment from draining down the patient's throat. This is conventionally done by a combination of nasal packing using gauze or other absorbent material and a hand held suction tube. The packing can become saturated with fluid and allow drippage or require changing. The hand held suction device requires an operator which slows the procedure and may require additional surgical personnel.

It is an object of the invention to provide a swab device for use in surgery, particularly microsurgery, to remove excess fluid by continuously and gently wicking fluid away from tissue and into a pad where it is subsequently removed by suction.

It is another object of the invention to provide a swab device for use in surgery to remove excess fluid which can be readily trimmed to any desired size and shape.

It is another object of the invention to provide a swab device for use in surgery to remove excess fluid which can be used throughout an operation without requiring replacement due to saturation or clogging.

It is another object of the invention to provide a swab device for use in surgery to remove excess fluid which will not damage delicate tissue it contacts.

It is another object of the invention to provide a flexible sterile platform for use in surgery, which removes excess fluid from its work surface by continuously and gently wicking fluid away into an integral pad where a suction tube subsequently removes it.

It is another object of the invention to provide a platform for use in surgery which removes fluid contacting its back side by gently wicking fluid into an integral pad where a suction tube subsequently removes it.

It is another object of the invention to provide a platform for use in surgery which can by oriented in any position.

It is another object of the invention to provide a platform for use in surgery which maintains a stable position and is slip-resistant on the tissue on which it is placed.

It is another object of the invention to provide a platform for use in surgery which is readily trimable to any desired size and shape.

It is another object of the invention to provide a device for nasal surgery which seals off the nose from the throat.

It is another object of the invention to provide a device for nasal surgery which prevents drainage of blood from the operational field down the back of the patient's throat.

It is another object of the invention to provide a device for nasal surgery which remove excess fluid by continuously and gently wicking fluid away from tissue and into a pad where a suction tube removes it.

SUMMARY OF THE INVENTION

The apparatus of the present invention provides a flexible, sterile, trimable device which gently and continuously removes unwanted fluid from an operating field during microsurgery or nasal surgery. The invention basically comprises a mat with a high wicking property, and a flexible tube with one end embedded in the mat. A preferred mat material is rayon felt. The embedded end of the tube has at least one hole through which suction is applied to the mat when the other end of the tube is attached to a suction source. The high wicking property of the mat allows fluid to be gently and efficiently removed from a site without the suction source being in direct contact with the pooling fluid. Suction removes fluid from the mat thereby preventing it from becoming saturated.

One embodiment of the present invention is as a platform for microsurgery. A membrane having a plurality of holes is applied to one side of the mat. The membrane provides the work surface to support the tissue on which microsurgery is performed, and it preferably is of a color contrasting with body tissue. Excess fluid on the membrane drains through holes where it is wicked into the mat and subsequently removed by the suction tube. Since the platform uses wicking action rather than gravity to remove fluid from its work surface, the platform can be used in any orientation. The platform allows evacuation of fluid from both sides of platform. The wicking action of the mat keeps the back side of the platform from becoming slippery so that the platform does not slip from the position where it is placed.

Another embodiment of the present invention is as a swabber. One end of a semi-rigid tube is embedded in the mat and the other end is connected to a flexible tube which is in turn connected to a suction source.

Another embodiment of the invention is as a device used in nasal surgery. A sheet of silicone rubber or similiar material is applied to one side of the mat. The sheet is non-porous and flexible, but sufficiently thick to give the device a springy quality. The device is folded longitudinally with the sheet on the inside and the embedded tube at the apex of the fold and inserted into a nasal cavity where it opens into an inverted V shape which lodges against tissue and seals the nose from the throat. The device prevents fluid from the nasal operation from draining down the back of the throat by continuously wicking fluid falling on the device into the mat where it is subsequently removed by the embedded suction tube.

BRIEF DESCRIPTION OF THE DRAWINGS

FIG. 4 is a longitudinal sectional view taken along line 4—4 of FIG. 1.

FIG. 5 is a cross sectional view taken along line 5—5 of FIG. 1.

FIG. 6 is a perspective view of a an embodiment of the present invention as a swabbing device used for microsurgery.

FIG. 7 is a perspective view of the swab end of a device of FIG. 6.

FIG. 8 is a longitudinal sectional view taken along line 6—6 of FIG. 6.

FIG. 9 is a perspective view of a an embodiment of the present invention as a device used for nasal surgery.

FIG. 10 is a longitudinal sectional view taken along line 10—10 of FIG. 9.

FIG. 11 is an illustration of how a device of FIG. 9 is installed in a nasal cavity.

FIG. 12 is a cross sectional view of a device of FIG. 9 in its installed position of FIG. 11.

DESCRIPTION OF THE PREFERRED EMBODIMENTS

Figure 1:
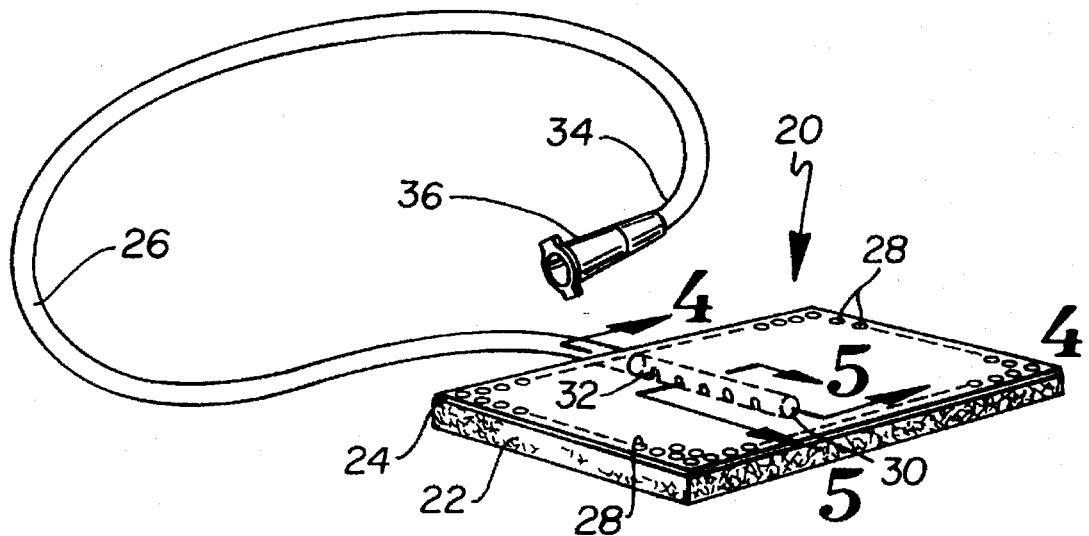
FIG. 1 is a perspective view of a an embodiment of the present invention as a platform for microsurgery.

Referring to the drawings, wherein like reference numerals designate like or similar elements throughout, one embodiment of the invention as a platform for microsurgery is illustrated in FIGS. 1 through 5, a second embodiment as a swabber is illustrated in FIGS. 6 through 8, and a third embodiment as a device for nasal cavity surgery is illustrated in FIGS. 9 through 12.

Microsurgery Platform

Referring to FIG. 1 a microsurgery platform 20 is used to isolate the structure on which microsurgery is to be performed, such as a blood vessel or nerve from surrounding tissue and provide a clean firm surface on which to work. The present invention provides a flexible, sterile microsurgery platform comprised of a wicking mat 22, a perforated membrane 24 attached to one side of mat 22, and a flexible tube 26 having a terminal end 30 embedded in mat 22. Typical sizes of platform 20 range from a 1" by 2" rectangle to a 4" by 6" rectangle, but platform 20 can be readily trimmed to any size and shape needed. Mat 22 is made of a material, preferably such as rayon felt, which has a high wicking property. The preferred embodiments of the invention use a rayon felt, such as orange SUNTEX™ from Solar United National Products, Inc., which is approximately 2 mm thick. Blood clotting can be inhibited in the mat by heparinizing it before use. Membrane 24 is thin, flexible and has a plurality of holes 28 perforating it which allow fluid passage through membrane 22 into mat 24. The holes can be made with a regular pattern and spacing which allows the surgeon, by knowing the distance between the holes, to gage the size of the vessels or other tissue being worked on. Membrane 22 may also be colored, preferably green, to contrast with tissue being worked on. In the preferred embodiment, membrane 22 is made of colored plastic tape adhesively bonded to mat 22.

Tube 26 has a terminal end 30 which is embedded in mat 22 and has one or more holes 32 at or near terminal end 30. Tube 26 has another end 34 which may have a fitting 36 adapted to connect to a suction device (not shown).

In use, fluid either drains through holes 28 in membrane 24 to contact mat 22, or it contacts mat 22 directly at its exposed surfaces. Mat 22 wicks fluid into it from its surface. fluid is removed from mat 22 by suction in tube 26 causing fluid to flow from mat 22 through holes 32 into tube 26 where it is carried away. Since fluid in a section of mat 22 in the immediate vicinity of holes 32 has been evacuated, wicking action of mat 22 causes fluid to flow from surrounding areas of mat 22 toward a section where tube 26 is embedded in mat 22.

The advantages of microsurgery platform 20 are that the wicking action of mat 22 conducts fluid to holes in tube 26 so that tube 26 need not be in direct contact with pooling fluid to evacuate it. This provides much greater flexibility in positioning platform 20 compared to other platforms which must be positioned so that fluid will run by gravity to evacuation holes. The construction of platform 20 allows evacuation of fluid from both sides of platform 20, whereas conventional platforms must pool fluid on the top side to evacuate it. Furthermore, platform 20 does not slip from the position where it is placed as do other platforms made of nonporous materials. Also, mat 22 acts as a buffer for the suction force emanating from tubing 26. Direct suction, even though very low power, can severely damage very delicate nerves and vessels typically exposed during microsurgery if those tissues come in contact with direct suction.

Figure 2:
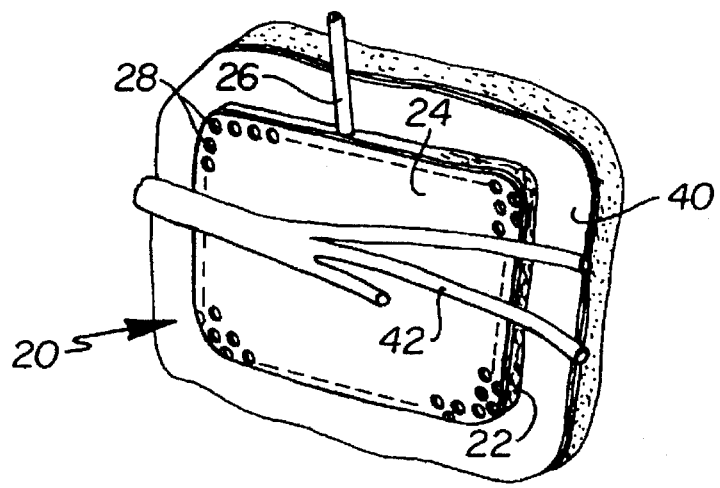
FIG. 2 is an illustration of a device of FIG. 1 as used in microsurgery.

Referring to FIG. 2, microsurgery platform 20 is shown as used to perform microsurgery on vessel 40. Platform 20 can be trimmed to any size or shape needed. The side of platform 20 with mat 22 exposed is placed against tissue 40. Wicking action keeps the interface between mat 22 and tissue 40 dry enough that platform 20 tends to stay in place even when used in a vertical orientation as shown in FIG. 2. The orientation of platform 20 and tube 26 can be in any direction since it does not depend on gravity to function. Also as shown in FIG. 2, platform 20 is flexible enough to easily curve to the natural shape of many tissues. Platform 20 is inserted between the structure on which microsurgery is to be performed, vessel 42 in this illustration and the underlying tissue 40. The contrasting color, preferably green, of membrane 24 and vessel 42 give the surgeon a good visual field on which to operate. Membrane 24 also remains clear of excessive fluid during surgery. Fluid from vessel 42 or the surrounding tissue does not accumulate on membrane 24 since fluid on membrane 24 goes through holes 28 and into mat 22 where it is wicked away and subsequently evacuated by tube 26.

Figure 3:
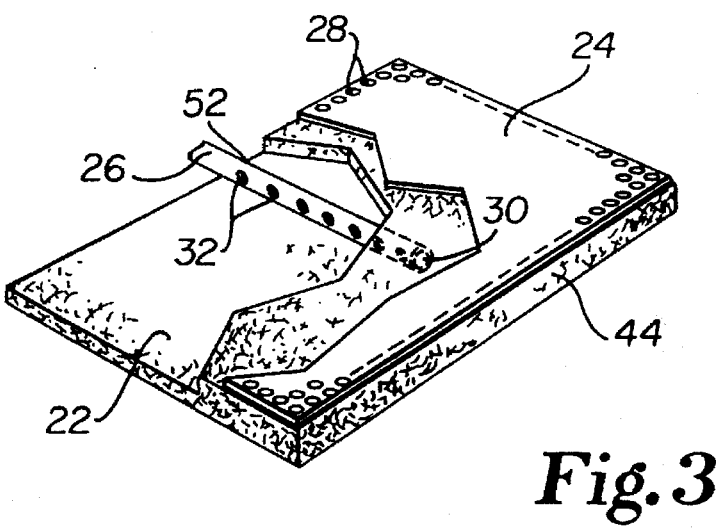
FIG. 3 is a partially exploded view of a device of FIG. 1.

Referring to FIG. 3, tube 26 is embedded in mat 22 such that terminal end 30 of tube 26 does not extend to edge 44 of mat 22 and all holes 32 are inside mat 22. An adhesive (not shown), such as silicone, is applied at point 52 where tube 26 exits mat 22 to keep tube 26 in place.

Referring to FIGS. 4 and 5, when tube 26 is inserted into mat 22, it forces a portion 50 of mat 22 to bulge out. The thickness 46 of bulging portion 50 of mat 22 is approximately equal to thickness 48 of mat 22 opposite bulging portion 50. It is preferable but not necessary that holes 32 be oriented as shown in the plane of mat 22. In the preferred embodiment membrane 24 is attached to mat 22 by an adhesive layer 38, but it is possible that membrane 24 could be attached to mat 22 by other means such as thermal bonding.

Surgical Swabber

Referring to FIG. 6, another embodiment of the invention is shown as used as a swabber 120. A swabber is used to intermittently evacuate fluid from an operating field. Swabber 120 is comprised of a wicking mat 122, a semi-rigid tubular wand 124 having one end 130 terminate inside mat 122 and another end 128 attached to flexible tube 126. Tube 126 may have a flexible coupling 138 for attaching to end 128 of wand 124. The other end 134 of tube 126 has a fitting 136 adapted to connect to a suction device (not shown). Mat 22 is made of a material, preferably such as rayon felt, which has a high wicking property. Swabber 120 is much smaller than a conventional stick sponge and is designed to be gripped with the fingers, not the whole hand. Wand 124 can have various diameters and lengths with typical outer diameter ranging from approximately 1 to 2 mm and lengths ranging from 8 to 12 cm. In the preferred embodiment, mat 122 is approximately 2 mm thick and 5 to 10 mm wide by 10 to 20 mm long. It can be trimmed to any suitable size and shape.

Referring to FIGS. 7 and 8, end 130 of wand 124 is inserted approximately in the center of the thickness of mat 122 causing bulges 140 and 140 of approximately equal thickness in mat 122. Adhesive 144, preferably silicone, bonds wand 124 to edge 146 of mat 122. End 130 of wand 124 has one orifice 132 at end 130 through which suction is applied to mat 122.

As with the microsurgery platform described above, mat 122 wicks fluid into it from its surface. Fluid is removed from mat 122 by suction in wand 124 causing fluid to flow from mat 122 through hole 132 into wand 124 where it is carded away. Since fluid in a section of mat 122 in the immediate vicinity of hole 132 has been evacuated, wicking action of mat 122 causes fluid to flow from surrounding areas of mat 122 toward a section where wand 124 is embedded in mat 122. Therefore, fluid can be evacuated without wand 126 being in direct contact with pooling fluid to evacuate it. Also, mat 122 acts as a buffer for the suction force emanating from wand 124. Direct suction, even though very low power, can seriously damage very delicate nerves and vessels typically exposed during microsurgery if those tissues come in contact with direct suction. Furtherefore, small cannulas typically used for suction often plug with tissue and stop functioning. Mat 122 acts as a filter to prevent such tissue from entering wand 124 thereby preventing blockage of wand 124 or tube 126. One swabber 120 can eliminate the need for dozens of cotton tipped applicators or similar devices typically used to swab fields during microsurgery. It also reduces the time needed to swab a field since swabber 120 is held in place until the field is sufficiently clear of fluid, compared to repeatedly applying, removing, and changing cotton tipped applicators.

Nasal Surgery Device

Another embodiment of the invention is designed for use in nasal surgery. It is essentially the same as microsurgery platform 120 described above, except that perforated membrane 24 is replaced with a nonporous silicone rubber sheet.

Referring to FIGS. 9 and 10, device 220 is comprised of wicking mat 222, a sheet 224 attached to one side of mat 222 and a flexible tube 226 having a terminal end 230 embedded in mat 222. Mat 222 is made of a material, preferably such as rayon felt, which has a high wicking property. Sheet 224 is non porous and flexible, but sufficiently thick to give device 220 a springy quality. Sheet 224 is preferably made of silicone rubber and in the preferred embodiment is between 0.5 and 1 mm thick. Device 220 typically has a rectangular shape approximately 25 mm by 50 mm but it can be readily trimmed to any size and shape needed. Sheet 224 is attached to mat 222 by adhesive 238, preferably silicone. Tube 226 has a terminal end 230 which is embedded in mat 222 and has one or more holes 232 at or near terminal end 230. Tube 226 has another end 234 which may have a fitting 236 adapted to connect to a suction device (not shown).

Tube 226 is embedded in mat 222 such that terminal end 230 of tube 226 does not extend to edge 244 of mat 222 and all holes 232 are inside mat 222. An adhesive (not shown), such as silicone, is applied at point 252 where tube 226 exits mat 222 to keep tube 226 in place.

When tube 226 is inserted into mat 222 it forces a portion 250 of mat 222 to bulge out. The thickness 246 of bulging portion 250 of mat 222 is approximately equal to thickness 248 of mat 222 opposite bulging portion 250. It is preferable but not necessary that holes 232 be oriented as shown in the plane of mat 222. For this embodiment it is possible that the tube be located between mat 222 and sheet 224 rather than embedded in mat 222.

Mat 222 wicks fluid into it from its surface. Fluid is removed from mat 222 by suction in tube 226 causing fluid to flow from mat 222 through holes 232 into tube 226 where it is carded away. Since fluid in a section of mat 222 in the immediate vicinity of holes 232 has been evacuated, wicking action of mat 222 causes fluid to flow from surrounding areas of mat 22 toward a section where tube 226 is embedded in mat 222.

Referring to FIGS. 11 and 12, in use, device 220 is folded into an inverted V as shown with sheet 224 on the inside of the V and tube 226 at the apex 240 of the V. It is lodged into position between the floor 262 of the nose and the back of the nasal cavity. Device 220 functions to seal off the nose from the throat so that blood from the nasal procedure in cavity 260 will not go down the back of the throat. Device 220 replaces conventional nasal packing and hand held suction cannula.

Device 220 is inserted along the floor 262 of the nose by folding it in half longitudinally with tube 226 being the fold line. When in position its inherent springy quality opens device 220 to an inverted V shape as shown where edges 252 and 254 contact walls of the nasal cavity 260.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A device for removing excess fluid during surgical procedures, comprising:
    (a) a flexible mat having a high wicking property: and
    (b) a flexible tube having a substantially straight end section embedded in said mat, said tube having at least one hole in said embedded end section, and
    (c) a flexible, nonporous sheet attached to one side of said mat, said sheet rendering the device elastic, whereby the device is used according to the following methodology:
        (i) said device is folded along said substantially straight embedded end section of said tube with said sheet on the inside;
        (ii) said folded device is inserted into a nasal cavity of a patient and positioned behind the base of nose; and
        (iii) said device unfolds into an inverted V shape that lodges in said nasal cavity and seals the nose from the throat, thereby preventing fluid from surgical procedure in the nose from draining down the throat.

2. The device of claim 1 wherein said embedded end section of said tube and a length extending from said mat is semi rigid.

3. The device of claim 2, wherein a flexible tube is attached to an end opposite said embedded end of said semi rigid tube.

4. The device of claim 1 further comprising a membrane attached to one side of said mat wherein said membrane has a plurality of holes passing through said membrane.

5. The device of claim 4 wherein said membrane is colored to contrast with body tissue.

6. The device of claim 1 wherein said mat is comprised of rayon felt.

* * * * *